(12) United States Patent
Kuras et al.

(10) Patent No.: US 8,956,412 B2
(45) Date of Patent: Feb. 17, 2015

(54) ARTIFICIAL DISC

(75) Inventors: James M. Kuras, Macedonia, OH (US); Raymond S. Ross, Sale (GB); Keith Duke, Cleveland, OH (US)

(73) Assignee: Axiomed, LLC, Beverly, MA (US)

( * ) Notice: Subject to any disclaimer, the term of this patent is extended or adjusted under 35 U.S.C. 154(b) by 2000 days.

(21) Appl. No.: 11/821,241

(22) Filed: Jun. 22, 2007

(65) Prior Publication Data
US 2008/0319548 A1 Dec. 25, 2008

(51) Int. Cl.
*A61F 2/44* (2006.01)
*A61F 2/30* (2006.01)

(52) U.S. Cl.
CPC ....... *A61F 2/442* (2013.01); *A61F 2002/30331* (2013.01); *A61F 2002/30367* (2013.01); *A61F 2002/30563* (2013.01); *A61F 2002/30884* (2013.01); *A61F 2220/0033* (2013.01)
USPC .................................................... 623/17.11

(58) Field of Classification Search
CPC ........ A61F 2/442; A61F 2/4425; A61F 2/443
USPC ........................................... 623/17.11–17.16
See application file for complete search history.

(56) References Cited

U.S. PATENT DOCUMENTS

| | | | |
|---|---|---|---|
| 4,759,766 A * | 7/1988 | Buettner-Janz et al. ... | 623/17.15 |
| 4,821,765 A | 4/1989 | Iqbal et al. | |
| 5,401,269 A * | 3/1995 | Buttner-Janz et al. ..... | 623/17.15 |
| 5,534,030 A * | 7/1996 | Navarro et al. ............ | 623/17.15 |
| 5,683,465 A * | 11/1997 | Shinn et al. ................ | 623/17.14 |
| 5,893,889 A * | 4/1999 | Harrington ................ | 623/17.16 |
| 6,063,121 A * | 5/2000 | Xavier et al. ............... | 623/17.15 |
| 6,368,350 B1 * | 4/2002 | Erickson et al. ........... | 623/17.14 |
| 6,419,704 B1 * | 7/2002 | Ferree ......................... | 623/17.12 |
| 6,579,320 B1 * | 6/2003 | Gauchet et al. ............ | 623/17.15 |
| 6,607,558 B2 | 8/2003 | Kuras | |
| 7,060,099 B2 * | 6/2006 | Carli et al. ................. | 623/17.14 |
| 7,128,761 B2 * | 10/2006 | Kuras et al. ................ | 623/17.15 |
| 7,169,181 B2 | 1/2007 | Kuras | |
| 7,201,776 B2 * | 4/2007 | Ferree et al. ............... | 623/17.16 |
| 7,250,060 B2 * | 7/2007 | Trieu ......................... | 623/17.15 |
| 7,442,211 B2 * | 10/2008 | de Villiers et al. ......... | 623/17.14 |
| 7,637,955 B2 * | 12/2009 | Marik et al. ................ | 623/17.14 |
| 7,682,396 B2 * | 3/2010 | Beaurain et al. ........... | 623/17.14 |
| 7,842,089 B2 * | 11/2010 | Aaron ........................ | 623/17.16 |
| 8,021,427 B2 * | 9/2011 | Spoonamore .............. | 623/17.14 |
| 2002/0035400 A1* | 3/2002 | Bryan et al. ................ | 623/17.15 |
| 2003/0074076 A1* | 4/2003 | Ferree et al. ............... | 623/17.16 |
| 2003/0176923 A1* | 9/2003 | Keller et al. ................ | 623/17.14 |

(Continued)

*Primary Examiner* — Mary Hoffman
(74) *Attorney, Agent, or Firm* — AKC Patents, LLC; Aliki K. Collins

(57) ABSTRACT

An artificial disc includes an intermediate section which is disposed between upper and lower retainers. The intermediate section includes a first portion which resists rotation of one of the retainers, for example, the upper retainer, from a first position to a second position. A second portion of the intermediate section of the artificial disc resists rotation of the upper retainer from the second position to a third position. The second portion of the intermediate section of the artificial disc is ineffective to provide significant resistance to relative rotation between the retainers during rotation of the upper retainer relative to the lower retainer from the first position to the second position. The artificial disc may be provided with projections which engage protrusions on the intermediate section to resist rotation of the upper retainer relative to the lower retainer from the second position to the third position.

30 Claims, 6 Drawing Sheets

(56) References Cited

U.S. PATENT DOCUMENTS

| | | | |
|---|---|---|---|
| 2003/0220691 A1* | 11/2003 | Songer et al. | 623/17.14 |
| 2003/0233146 A1* | 12/2003 | Grinberg et al. | 623/17.14 |
| 2004/0024460 A1* | 2/2004 | Ferree | 623/17.12 |
| 2004/0024461 A1* | 2/2004 | Ferree | 623/17.13 |
| 2004/0030398 A1* | 2/2004 | Ferree | 623/20.32 |
| 2004/0054411 A1* | 3/2004 | Kelly et al. | 623/17.13 |
| 2004/0068321 A1 | 4/2004 | Ferree | |
| 2004/0093087 A1* | 5/2004 | Ferree et al. | 623/17.13 |
| 2004/0127991 A1* | 7/2004 | Ferree | 623/17.11 |
| 2004/0133281 A1* | 7/2004 | Khandkar et al. | 623/17.16 |
| 2004/0143332 A1* | 7/2004 | Krueger et al. | 623/17.14 |
| 2004/0193273 A1* | 9/2004 | Huang | 623/17.12 |
| 2004/0243240 A1* | 12/2004 | Beaurain et al. | 623/17.14 |
| 2004/0267364 A1* | 12/2004 | Carli et al. | 623/17.14 |
| 2005/0021146 A1* | 1/2005 | de Villiers et al. | 623/17.15 |
| 2005/0038516 A1* | 2/2005 | Spoonamore | 623/17.14 |
| 2005/0043803 A1* | 2/2005 | Schultz et al. | 623/17.16 |
| 2005/0228500 A1 | 10/2005 | Kim et al. | |
| 2005/0256581 A1 | 11/2005 | Songer et al. | |
| 2006/0041314 A1* | 2/2006 | Millard | 623/17.16 |
| 2006/0089714 A1* | 4/2006 | Liu et al. | 623/17.11 |
| 2006/0095132 A1* | 5/2006 | Kirschman | 623/17.14 |
| 2006/0111783 A1* | 5/2006 | Aflatoon et al. | 623/17.14 |
| 2006/0155377 A1* | 7/2006 | Beaurain et al. | 623/17.15 |
| 2006/0235526 A1* | 10/2006 | Lemaire | 623/17.14 |
| 2006/0235530 A1* | 10/2006 | Shelokov | 623/17.15 |
| 2006/0259144 A1* | 11/2006 | Trieu | 623/17.13 |
| 2007/0050032 A1* | 3/2007 | Gittings et al. | 623/17.12 |
| 2007/0088441 A1* | 4/2007 | Duggal et al. | 623/17.16 |
| 2007/0233262 A1* | 10/2007 | Arnin et al. | 623/17.15 |
| 2007/0276495 A1* | 11/2007 | Aaron | 623/17.12 |
| 2008/0183296 A1* | 7/2008 | Ferree | 623/17.16 |
| 2009/0204219 A1* | 8/2009 | Beaurain et al. | 623/17.16 |
| 2010/0036497 A1* | 2/2010 | Lechmann et al. | 623/17.16 |
| 2010/0249936 A1* | 9/2010 | Bertagnoli | 623/17.16 |
| 2011/0054617 A1* | 3/2011 | Sekhon et al. | 623/17.13 |

* cited by examiner

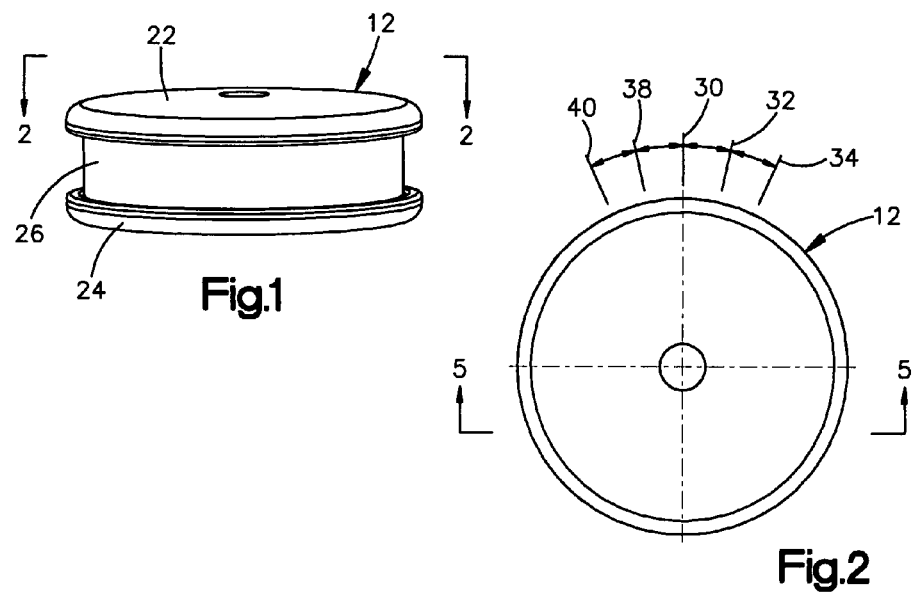
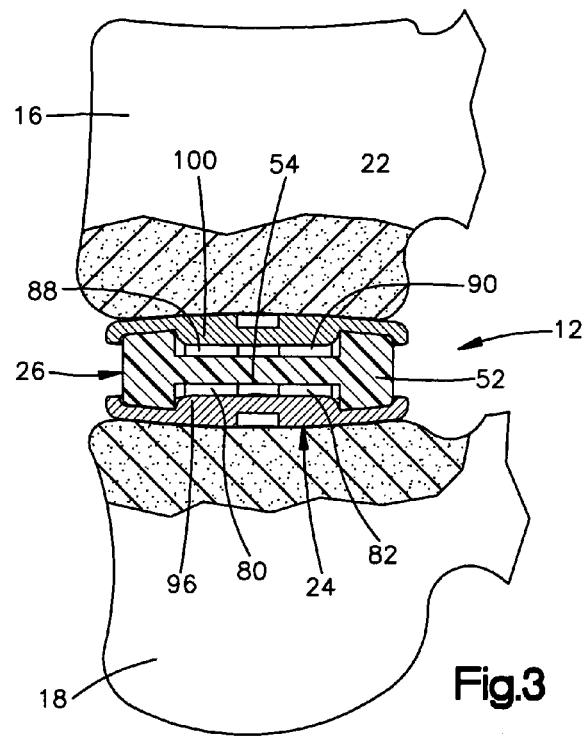

ARTIFICIAL DISC

FIELD OF THE INVENTION

The present invention relates to an artificial disc to replace a damaged spinal disc in a spinal column.

BACKGROUND OF THE INVENTION

Known artificial discs are disclosed in U.S. Pat. Nos. 6,607,558; 7,128,761; and 7,169,181. These patents disclose artificial discs having retainers which are engagable with vertebrae. The retainers are connected with an intermediate section which is disposed between the retainers. Relative rotation between the vertebrae is resisted by the intermediate section of the artificial disc. The entire intermediate section of the artificial disc is effective to resist relative rotation between the vertebrae throughout the range of relative rotation between the vertebrae.

SUMMARY OF THE INVENTION

An improved artificial disc to replace a damaged spinal disc in a spinal column includes a first retainer which is engagable with a first vertebra and a second retainer which is engagable with a second vertebra. An intermediate section is connected with the first and second retainers. The intermediate section of the artificial disc resists relative rotation between the first and second retainers.

The intermediate section includes a first portion which resists relative rotation between the first and second retainers from a first position to a second position. A second portion of the intermediate section resists relative rotation between the first and second retainers from the second position to a third position. The second portion of the intermediate section of the artificial disc is ineffective to provide significant resistance to relative rotation between the first and second retainers from the first position to the second position.

The intermediate section of the artificial disc may include a ring which is connected with the first and second retainers to resist relative rotation between the retainers. A plurality of protrusions may extend inwardly from the ring toward a central portion of the intermediate section. A plurality of projections on the retainers are engagable with the protrusions. The projections on the retainer may have longitudinal axes which extend from central portions of the retainers toward peripheral portions of the retainers.

An artificial disc having many different features is disclosed herein. These features may be used in combination with each other as disclosed herein. Alternatively, the features may be used separately or in combination with known features from the prior art. For example, the intermediate section of the artificial disc may have any one of many different constructions. As another example, the retainers may have any one of many different constructions.

BRIEF DESCRIPTION OF THE DRAWINGS

The foregoing and other features of the present invention will become apparent to one skilled in the art to which the invention relates upon consideration of the following description of the invention with reference to the accompanying drawings in which:

FIG. 1 is a schematic side elevational view of an artificial disc constructed in accordance with the present invention;

FIG. 2 is a schematic plan view, taken generally along the line 2-2 of FIG. 1, further illustrating the artificial disc;

FIG. 3 is a fragmentary schematic sectional illustration depicting the manner in which the artificial disc of FIGS. 1 and 2 is utilized to replace a damaged spinal disc in a spinal column;

DESCRIPTION OF EMBODIMENTS OF THE INVENTION

Figure 4:
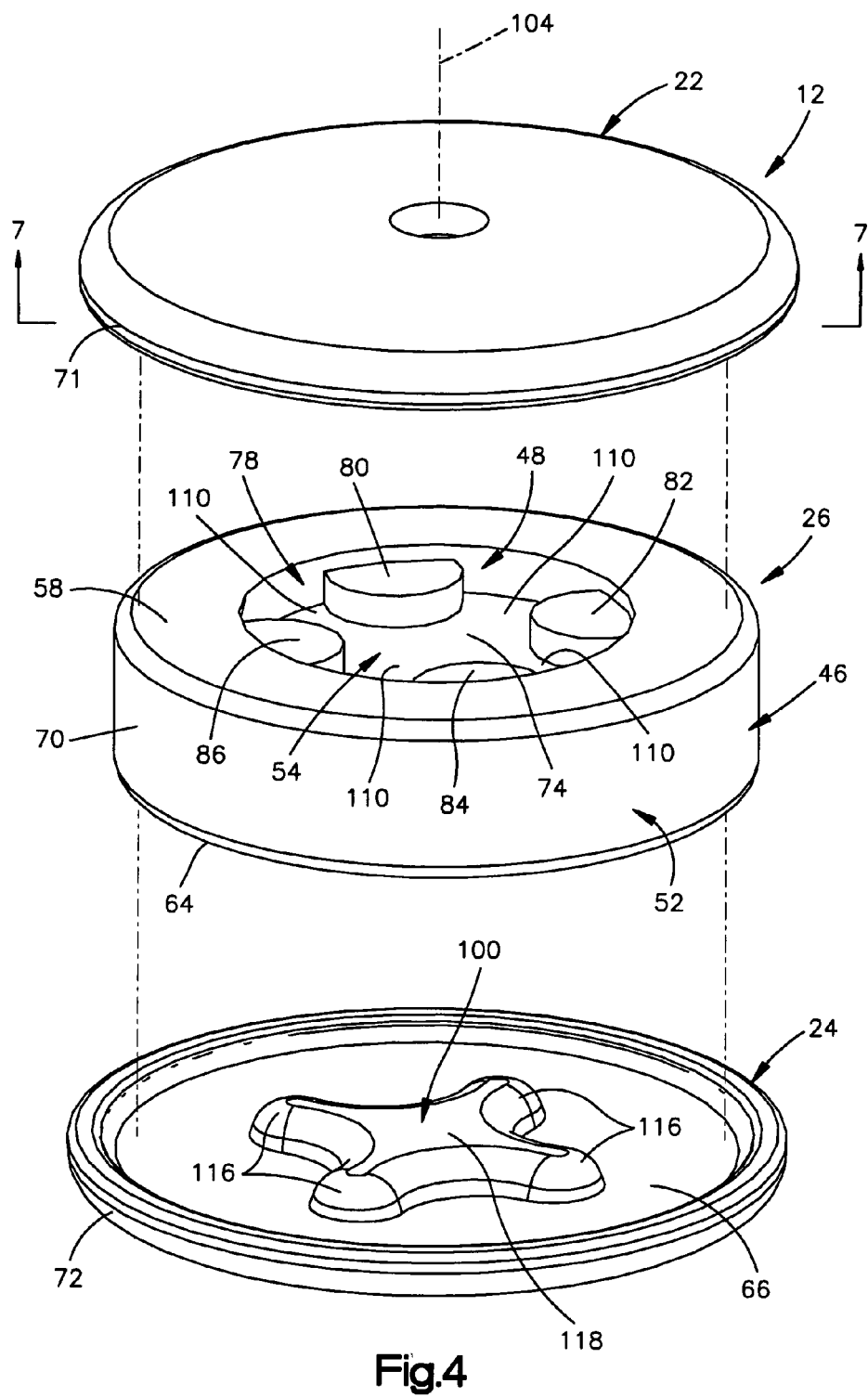
FIG. 4 is an exploded, schematic perspective view of the artificial disc of FIGS. 1 and 2 depicting the construction of upper and lower retainers and an intermediate section which is disposed between the retainers.

An artificial disc 12 (FIGS. 1-3) is to replace a damaged spinal disc in a spinal column. Thus, the artificial disc 12 is mounted between upper and lower vertebrae 16 and 18 (FIG. 3). The artificial disc 12 is intended to replace a damaged or degenerated cervical vertebra. However, the artificial disc 12 may be utilized to replace a damaged disc in a different location in a patient's spine, such as a thoracic vertebra or a lumbar vertebra.

The artificial disc 12 includes upper and lower retainers 22 and 24 (FIG. 1) which are fixedly connected to an intermediate section 26. The intermediate section 26 forms a resilient core which is secured to the upper and lower retainers 22 and 24. The upper and lower retainers 22 and 24 are secured to the upper and lower vertebrae 16 and 18 (FIG. 3) During relative rotation between the upper and lower vertebrae 16 and 18, the upper retainer 22 moves with the upper vertebra 16 and the lower retainer 24 moves with the lower vertebra 18.

Although the artificial disc 12 has been illustrated as having a circular configuration (FIG. 2), it is contemplated that the artificial disc may have a different configuration if desired. For example, the artificial disc 12 may have a configuration which corresponds to the configuration of the portions of the upper and lower vertebrae 16 and 18 to be engaged by the artificial disc 12. Alternatively, the artificial disc 12 may have a generally oval or a polygonal configuration.

The intermediate section 26 resiliently resists relative movement between the retainers 22 and 24. The resiliently deflectable intermediate section 26 enables the rigid upper and lower retainers 22 and 24 to move vertically (as viewed in FIG. 1) relative to each other. In addition, the resiliently deflectable intermediate section 26 enables the rigid upper and lower retainers 22 and 24 to rotate relative to each other in either a clockwise or counterclockwise direction, as viewed in FIG. 2.

The intermediate section 26 is resiliently deformed by relative movement between the upper and lower retainers 22 and 24. Therefore, when a force (torque) tending to rotate one of the retainers, 22 or 24 relative to the other retainer is applied to the artificial disc 12 by the vertebrae 16 and 18, the intermediate section 26 is resiliently deflected. When this force (torque) is interrupted, resilient recovery or spring back of the intermediate section 26 returns the retainers 22 and 24 to their initial positions relative to each other.

Assuming that a clockwise force is applied to the upper retainer 22 to rotate it relative to the lower retainer 24, the upper retainer will rotate from an initial or first position 30 (FIG. 2) toward a second position 32. During this relative rotation between the upper and lower retainers 22 and 24, the intermediate section 26 is effective to resiliently resist relative rotation between the retainers. As the upper retainer 22 rotates from the first position 30 toward the second position 32, the extent of resilient deflection of the intermediate section 26 increases. As this occurs, the force with which the intermediate section 26 resiliently resists movement of the upper retainer 22 relative to the lower retainer 24 increases. With each increment of rotation of the upper retainer 22 from the first or initial position 30 toward the second position 32, there is an incremental increase in the force resisting relative rotation between the retainers.

As the upper retainer 22 continues to rotate in a clockwise direction (as viewed in FIG. 2) relative to the lower retainer 24, the upper retainer moves from the second position 32 toward a third position 34. As the upper retainer 22 begins to rotate from the second position 32, the intermediate section 26 resists rotation of the upper retainer 22 relative to the lower retainer 24 with a force which increases at an increasing rate with each increment of rotation of the upper retainer 22 relative to the lower retainer.

During each increment of clockwise rotation (as viewed in FIG. 2) of the upper retainer 22 relative to the lower retainer 24 from the first position 30 to the second position 32, the force resisting relative movement between the upper and lower retainers 22 and 24 increases by a first incremental amount. During each increment of rotation of the upper retainer 22 relative to the lower retainer 24 from the second position 32 toward the third position 34, the force increases by an amount which is greater than the first incremental amount. The incremental amount by which the force increases with each increment of rotation between the second position 32 and third position 34 is greater than the incremental amount by which the force increases with each increment of rotation between the first position 30 and the second position 32.

It should be understood that the upper retainer 22 may be rotated in a counterclockwise direction (as viewed in FIG. 2) from the first position 30 to a fourth position 38 and from the fourth position 38 to a fifth position 40. The force resisting relative rotation between the upper and lower retainers 22 and 24 increases in the same manner as previously described in conjunction with clockwise rotation to the second and third positions 32 and 34. Thus, during movement of the upper retainer 22 from the first position 30 toward the fourth position 38, the force resisting relative rotation between the upper and lower retainers 22 and 24 increased by the aforesaid first incremental amount with each increment of relative rotation. During rotation of the upper retainer 22 from the fourth position 38 to the fifth position 40, the force resisting relative rotation between the upper and lower retainers 22 and 24 increases by an amount which is greater than the first incremental amount. As was previously mentioned, the second incremental amount of force is greater than the first incremental amount of force.

The intermediate section 26 of the artificial disc 12 includes a first or base portion 46 (FIGS. 4 and 5) and a second or protruding portion 48. The first or base portion 46 is connected to the upper and lower retainers 22 and 24. The first or base portion 46 is resiliently deflected upon the occurrence of relative rotation between the upper and lower retainers 22 and 24 throughout their range of rotation.

The first or base portion 46 of the intermediate section 26 is resiliently deflected to an increasing extent with each increment of rotation of the upper retainer 22 from the first position 30 (FIG. 2) through the second position 32 to the third position 34. Similarly, the first or base portion 46 is resiliently deflected to an increasing extent with each increment of rotation of the upper retainer 22 from the first position 30 through the fourth position 38 to the fifth position 40. When the force which is applied to the upper retainer 22 to rotate it relative to the lower retainer 24 is released, the resilience of the intermediate section 26 rotates the upper retainer 22 relative to the lower retainer 24 back to the first position 30.

The second or protruding portion 48 (FIGS. 4 and 5) of the intermediate section 26 is effective to resist clockwise (as viewed in FIG. 2) relative rotation between the upper and lower retainers 22 and 24 only after a predetermined amount of relative rotation has occurred. Thus, the second or protruding portion 48 is effective to resist relative rotation between the upper retainer 22 and lower retainer 24 during rotation of the upper retainer from the second position 32 (FIG. 2) to the third position 34. The second or protruding portion 48 is ineffective to provide significant resistance to relative rotation between the upper retainer 22 and the lower retainer 24 during rotation of the upper retainer from the first position 30 to the second position 32.

Similarly, the second or protruding portion 48 (FIGS. 5 and 6) of the intermediate section 26 is effective to resist counterclockwise (as viewed in FIG. 2) relative rotation between the upper retainer 22 and the lower retainer 24 during rotation of the upper retainer from the fourth position 38 (FIG. 2) to the fifth position 40. However, the second or protruding portion 48 is ineffective to provide significant resistance to relative rotation between the upper and lower retainers 22 and 24 during movement of the upper retainer from the first position 30 to the fourth position 38.

It should be understood that the positions 30, 32, 34, 38 and 40 illustrated in FIG. 2 for the upper retainer 22 relative to the lower retainer 24 are only a schematic illustration of the relative positions of the upper and lower retainers. The arcuate distance between the positions 30, 32, 34, 38 and 40 may be either larger or smaller than the illustrated distance. Furthermore, the arcuate distances between the positions 30, 32, 34, 38 and 40 may differ from each other. The arcuate distances illustrated have been set forth in FIG. 2 merely for purposes of clarity of illustration.

Regardless of the extent of the arcuate rotational distances between the positions 30, 32, 34, 38 and 40, relative rotation between the upper and lower retainers 22 and 24 is resisted by the first or base portion 46 of the intermediate section 26 throughout the range of relative rotation. The second or protruding portion 48 of the intermediate section 26 is effective to provide significance resistance to relative rotation between the upper and lower retainers 22 and 24 only during the final portions of the range of movement of the upper and lower retainers relative to each other. Although the foregoing description has assumed that the upper retainer 22 is rotated relative to the lower retainer 24, the lower retainer may be rotated relative to the upper retainer or both retainers may move relative to each other.

It should be understood that the second or protruding portion 48 of the intermediate section 26 may provide an insignificant amount of resistance to relative rotation between the upper and lower retainers 22 and 24 from the first position 30 to either the second position 32 or the fourth position 38. This insignificant resistance to relative rotation is less than ten percent of the resistance to relative rotation provided by the first or base portion 46 of the intermediate section 26. The small, insignificant resistance provided by the protruding portion 48 is a result of minor flexing of the protruding portion.

The first or base portion 46 (FIGS. 4 and 5) of the intermediate section 26 includes a ring or peripheral portion 52 and a web 54. The ring 52 extends around and encloses the web 54. The illustrated ring 52 and web 54 have circular configurations. However, the ring 52 and/or web 54 may have a noncircular configuration if desired.

An upper side surface 58 of the ring 52 is fixedly connected with a lower side surface 60 (FIG. 5) of the upper retainer 22. Therefore, upon relative rotation between the upper and lower retainers 22 and 24, the upper side surface 58 of the intermediate section 26 does not move relative to the lower side surface 60 of the upper retainer 22. The upper side surface 58 of the ring 52 may have a configuration which is different than the illustrated annular configuration. For example, the upper side surface 58 of the ring 52 may have an oval or polygonal configuration if desired.

Similarly, the ring 52 has a lower side surface 64 which may be parallel to the upper side surface 58. The lower side surface 64 of the ring 52 is fixedly connected to an upper side surface 66 (FIG. 4) of the lower retainer 24. Upon the occurrence of relative rotation between the upper retainer 22 and the lower retainer 24, the lower side surface 64 of the intermediate section 26 does not move relative to the upper side surface 66 of the lower retainer. The configuration and size of the lower side surface 64 may be the same or different than the configuration and size of the upper side surface 58.

Upon the occurrence of relative rotation between the upper retainer 22 and the lower retainer 24, the ring 52 is resiliently flexed. Thus, force is transmitted from the lower side surface 60 of the upper retainer 22 through the upper side surface 58 of the ring 52 to the intermediate section 26. Similarly, force is transmitted from the upper side surface 66 of the lower retainer 24 through the lower side surface 64 of the ring 52 to the intermediate section 26. This results in resilient deflection of the ring 52 and web 54 upon relative rotation between the upper and lower retainers 22 and 24.

Figure 5:
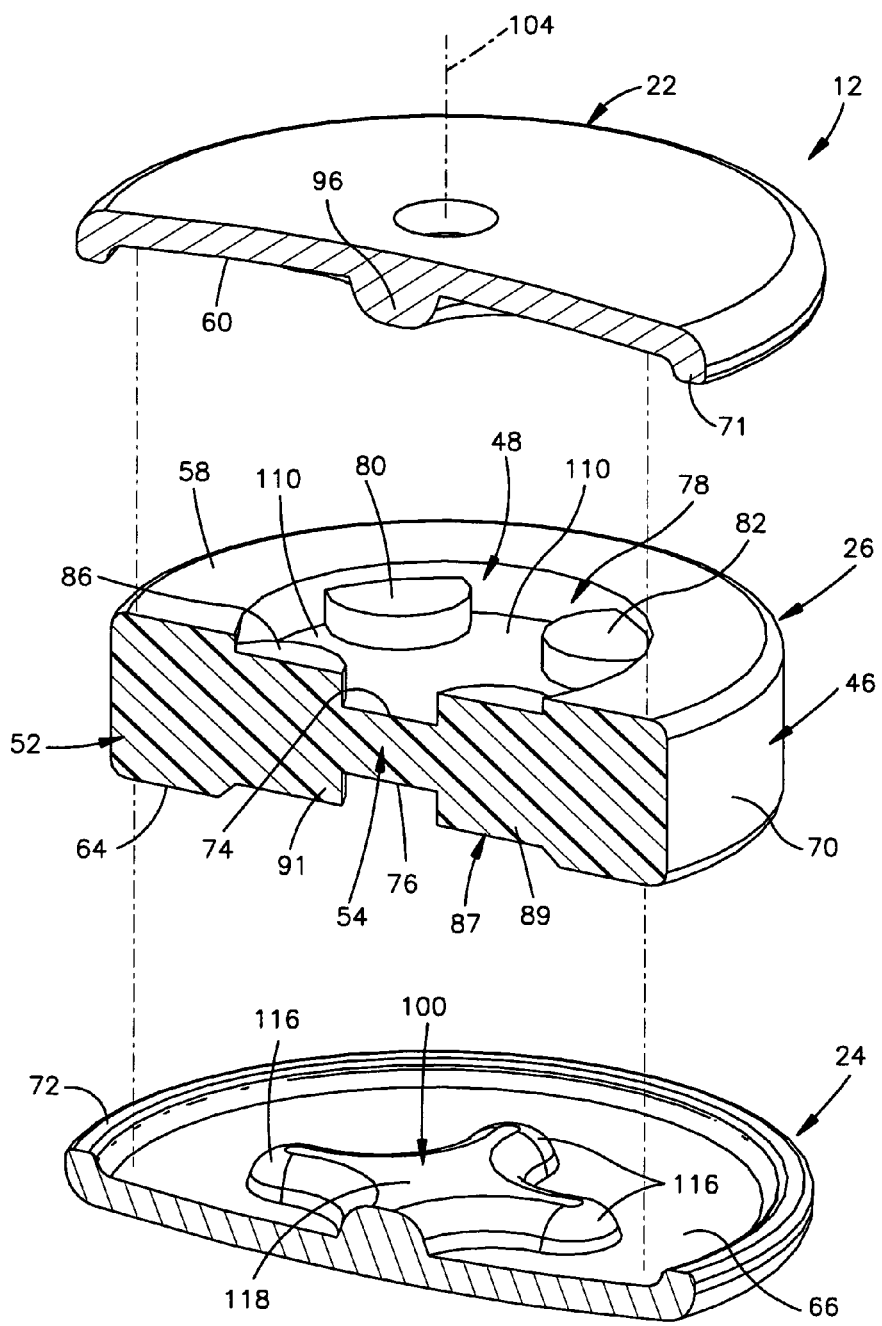
FIG. 5 is an exploded, schematic sectional view, taken generally along the line 5-5 of FIG. 2, further illustrating the construction of the artificial disc.

In the specific embodiment illustrated in FIGS. 4 and 5, the ring 52 has an annular configuration. The upper and lower side surfaces 58 and 64 of the ring 52 are of the same shape and size and are generally flat and parallel. The ring 52 has an outer side surface 70 which is formed as a portion of a cylinder. It should be understood that the ring 52 may have upper and lower side surfaces 58 and 64 and an outer side surface 70 with configurations which are different than the illustrated circular configurations. For example the upper and lower side surfaces 58 and 64 and the outer side surface 70 may have an oval or polygonal configuration. The flat circular upper and lower side surfaces 58 and 64 of the intermediate section 26 extend generally parallel to each other. However, the upper side surface 58 may slope axially downwardly (as viewed in FIG. 5) and radially outwardly. Similarly, the lower side surface 64 may slope axially upwardly and radially outwardly. If this is done, the lower side surface 60 of the upper retainer 22 would be provided with a slope which would correspond to the slope of the upper side surface 58 of the ring 52. Similarly, the upper side surface 66 of the lower retainer 24 would have a slope which corresponds to the slope of the lower side surface 64 of the ring 52.

Regardless of whether the upper and lower side surfaces 58 and 64 of the ring 52 are parallel to each other or slope radially relative to each other, the upper and lower side surfaces 58 and 64 of the ring are fixedly connected to the identical upper and lower retainers 22 and 24. The upper and lower retainers 22 and 24 have circular peripheral edge portions 71 and 72 (FIGS. 4 and 5) with diameters which are slightly greater than the diameter of the outer side surface 70 of the intermediate section 26. The ring 52 may be secured to the upper and lower retainers 22 and 24 by bonding or with a suitable cement. If desired, serrations, projections and/or teeth may be provided in the upper and lower retainers 22 and 24 to engage corresponding projections, serrations or teeth in the upper and lower side surfaces 58 and 64 of the ring 52.

The ring 52 is secured to the upper and lower retainers 22 and 24 so that the surfaces 58 and 62 on the ring 52 can not move relative to the surfaces to which they are connected on the retainers 22 and 24. Thus, the upper ring surface 58 (FIG. 5) is not movable relative to the lower side surface 60 on the upper retainer 22. Similarly, the lower ring surface 64 is not movable relative to the upper side surface 66 on the lower retainer 24. This results in the upper ring surface 58 being stationary relative to the lower side surface 60 on the upper retainer 22. Similarly, the lower ring surface 64 is stationary relative to the upper side surface on the lower retainer 24.

The web 54 (FIG. 5) is enclosed by the ring 52. The web 54 has a circular configuration with a flat imperforate upper side surface 74 and a flat imperforate lower side surface 76. The flat upper and lower side surfaces 74 and 76 of the web 54 extend parallel to each other and extend radially inwardly from the ring 52. Although the web 54 is imperforate, one or more openings may be provided in the web if desired.

The flat upper side surface 74 of the web 54 is located the same distance from the upper side surface 58 of the ring 52 as the lower side surface 76 of the web is located from the lower side surface 64 of the ring. Although the web 54 has a uniform thickness throughout its extent, the thickness of the web may vary. For example, the web 54 may be thicker at a peripheral portion of the web than at a central portion of the web.

Upon the occurrence of relative rotation between the upper retainer 22 and lower retainer 24 from the first position 30 (FIG. 2) to the second position 32, the ring 52 and web 54 are resiliently deflected. This resilient deflection of the ring 52 and web 54 occurs under the influence of force transmitted from the upper and lower retainers 22 and 24 to the ring 52. The ring 52 is resiliently deflected in a peripheral or circumferential direction, that is along the outer side surface 70, by the twisting action imparted to the ring by the upper and lower retainers 22 and 24. As the ring 52 is twisted or deflected, the web 54 is also twisted or deflected. Of course, the ring 52 and web 54 are deflected in the same manner when the upper and lower retainers 22 and 24 are rotated relative to each other from the first position 30 to the fourth position 38 (FIG. 2).

The ring 52, web 54, and retainers 22 and 24 all have a circular configuration and are disposed in a coaxial relationship. However, it is contemplated that the ring 52, and retainers 22 and 24 web 54 may have a different configuration if desired. For example, the ring 52 and web 54 may have a generally oval configuration. Alternatively, the ring 52, web 54, and retainers 22 and 24 may all have a configuration which is a function of the configuration of surface areas on the vertebrae 16 and 18 (FIG. 3) to be engaged by the upper and lower retainers 22 and 24.

The second or protruding portion 48 of the intermediate section 26 includes a first or upper array 78 of identical protrusions 80, 82, 84 and 86 (FIGS. 4 and 5). The protrusions 80-86 are disposed in a circular array and protrude axially upwardly from the upper side surface 74 of the web 54. The protrusions 80-86 all have the same, generally semicircular configuration and extend radially inwardly from the ring 52. The protrusions 80-86 have the same thickness, as measured vertically from the upper side surface 74 of the web 54, throughout the extent of the protrusions.

The second or protruding portion 48 also includes a second or lower array 87 (FIG. 6) of identical protrusions 88, 89, 90 and 91 which extend axially downwardly (as viewed in FIG. 5) from the lower side surface 76 of the web 54. The protrusions 88-91 (FIG. 6) in the lower array 87 of protrusions have the same configuration and size as the protrusions 80-86 in the upper array 78 of protrusions. The protrusions 80-86 in the upper array 78 of protrusions are vertically aligned, as viewed in FIGS. 4 and 5, with the protrusions 88-91 in the lower array 87 of protrusions.

The protrusions 80-86 and 88-91 have arcuate side surfaces which extend perpendicular to the upper and lower side surfaces 74 and 76 of the web 54. The protrusions 80-86 and 88-91 have flat, axially outer, end surfaces which extend parallel to the upper and lower side surfaces 74 and 76 of the web 54. However, the axially outer end surfaces on the protrusions 80-86 and 88-91 may extend transverse to the upper and lower side surfaces 74 and 76 of the web 54 if desired.

If desired, the protrusions 88-91 in the lower array 87 of protrusions may have a configuration and/or size which is different than the configuration and/or size of the protrusions 80-86 in the upper array 78 of protrusions. For example the protrusions 88-91 in the lower array 87 of protrusions may have a configuration which is different than the generally semicircular configuration illustrated in FIG. 6. The protrusions 88-91 in the lower array 87 of protrusions may be either larger or smaller than the protrusions 80-86 in the upper array 78 of protrusions.

A projection 96 (FIGS. 5 and 7) on the upper retainer 22 cooperates with the protrusions 80-86 of the upper array 78 of protrusions. Similarly, a projection 100 (FIGS. 4 and 5) on the lower retainer 24 cooperates with the lower array 87 (FIG. 6) of protrusions. The projections 96 and 100 have the same configuration and are vertically aligned with each other when the upper and lower retainers 22 and 24 are in the first position 30 (FIG. 2). At this time, the projections 96 and 100 are spaced from the protrusions in the upper and lower arrays 78 and 87 of protrusions.

Figure 6:
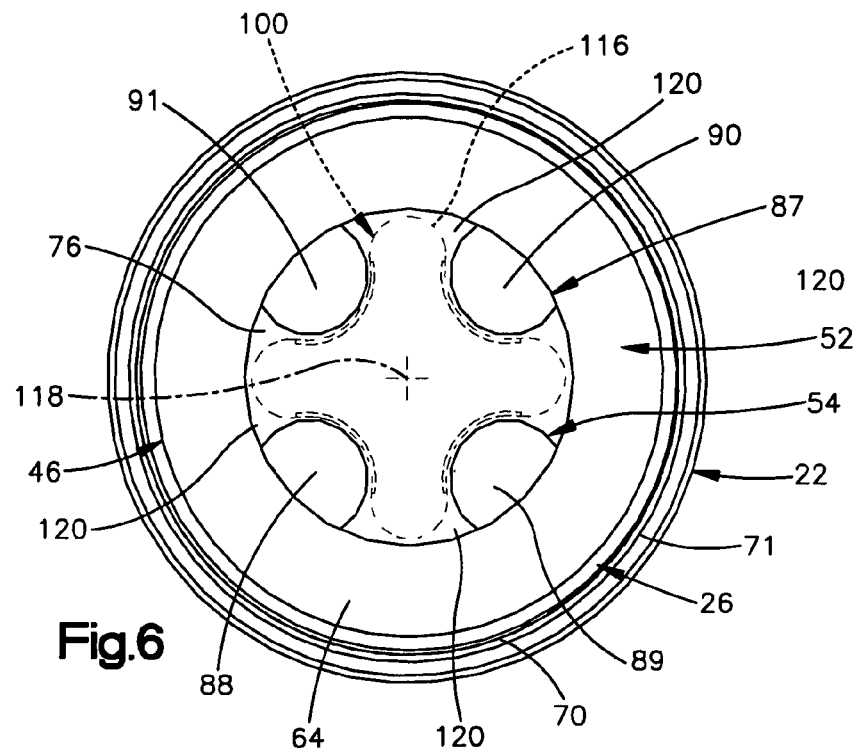
FIG. 6 is a schematic plan view, on a reduced scale, taken generally along the line 6-6 of FIG. 4, and further illustrating the construction of the intermediate section of the artificial disc.
Figure 7:
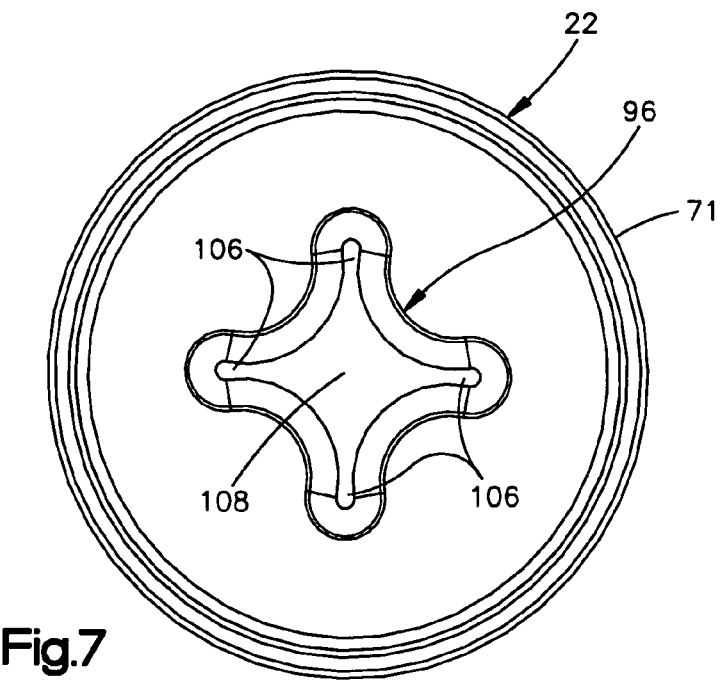
FIG. 7 is a schematic plan view, on a reduced scale, taken generally along the line 7-7 of FIG. 4 and further illustrating the construction of a retainer.

Upon the occurrence of relative rotation between the upper and lower retainers 22 and 24, the projections 96 and 100 rotate relative to each other about a central axis 104 of the artificial disc 12 and move into a non-aligned condition. During relative movement between the upper and lower retainers 22 and 24 from the first position 30 (FIG. 2) to the second position 32, the upper projection 96 (FIGS. 5 and 7) is spaced from or moves into engagement with the protrusions 80-86 in the upper array 78 of protrusions, including the protrusions 80-86. Similarly, the projection 100 (FIGS. 4 and 5) on the lower retainer 24 is spaced from or moves into engagement with the protrusions 88-91 in the lower array 87 of protrusions (FIG. 6). Therefore, during relative movement between the upper and lower retainers 22 and 24 from the first position 30 to the second position 32, the projections 96 and 100 are ineffective to deflect the protrusions of the upper and lower arrays 78 and 87 of protrusions.

When the upper and lower retainers 22 and 24 have rotated relative to each other, from the first position 30 (FIG. 2) to the second position 32, surfaces on the identical projections 96 and 100 will have moved into engagement with surfaces on the protrusions in the upper and lower arrays 78 and 87 of protrusions (FIGS. 4-7). Continued relative rotation between the upper and lower retainers 22 and 24 toward the third position 34 results in the protrusions 80-86 of the upper array 78 of protrusions being resiliently deflected by the projection 96 on the upper retainer 22. Similarly, the protrusions 88-91 in the lower array 87 of protrusions are resiliently deflected by the projection 100 on the lower retainer 24. Deformation of the upper and lower arrays 78 and 87 of protrusions by the upper projection 96 and lower projection 100 increases the resistance to relative rotation between the upper retainer 22 and lower retainer 24.

During relative movement between the upper retainer 22 and lower retainer 24 from the first position 30 to the second position 32, the projections 96 and 100 are spaced from the lower and upper arrays 78 and 87 of protrusions. Therefore, the only resistance to relative rotation between the upper and lower retainers 22 and 24 is provided by elastic deformation of the ring 52 and web 54. During relative movement between the upper and lower retainers 22 and 24 from the second position 32 (FIG. 2) toward the third position 34, the ring 52 and web 54 are elastically deformed. In addition, the upper and lower arrays 78 and 87 of protrusions are elastically deformed. Therefore, there is greater resistance to each increment of relative movement between the upper and lower retainers 22 and 24 during movement from the second position 32 to the third position 34 that is encountered for each increment of movement of the retainers from the first position 30 to the second position 32.

The upper and lower projections 96 and 100 (FIGS. 4, 5 and 7) have the same configuration. The upper projection 96 (FIG. 7) includes a plurality of arms 106. Each of the arms 106 has side surfaces which extend radially outward from a central portion 108 of the upper retainer 22 toward the circular peripheral edge portion 71 of the upper retainer. The side surfaces on each of the arms 106 extends into a space or recess 110 (FIGS. 4 and 5) between the protrusions 80-86 of the upper array 78 of protrusions.

When the upper and lower retainers 22 and 24 are in the first or initial position 30 (FIG. 2) relative to each other, the side surfaces on the arms 106 (FIG. 7) are spaced from the protrusions 80-86 (FIGS. 4 and 5) in the upper array 78 of protrusions. The side surfaces on the arms 106 face toward and are spaced apart from side surfaces on the protrusions 80-86 of the upper array 78 of protrusions when the upper and lower retainers 22 and 24 are in the first position 30. Although the side surfaces on the protrusions 80-86 extend perpendicular to the web 54, the side surfaces on the protrusions may be skewed relative to the upper side surface 74 of the web 54.

The lower projection 100 (FIGS. 4 and 5) includes a plurality of arms 116. Each of the arms 116 has side surfaces which extend radially outward from a central portion 118 of the lower retainer 24 toward the circular peripheral edge portion 72 of the lower retainer. The side surfaces on each of the arms 116 extends into a space or recess 120 (FIG. 6) between protrusions 88-91 of the lower array 87 of protrusions.

When the upper and lower retainers 22 and 24 are in the first or initial position 30 (FIG. 2) relative to each other, the side surfaces on the arms 116 (FIGS. 4 and 5) face toward and are spaced from side surfaces on the protrusions 88-91 of the lower array 87 of protrusions (FIG. 6). Although the side surfaces on the protrusions 88-91 extend perpendicular to the web 54, the side surfaces on the protrusions may be skewed relative to the lower side surface 76 of the web 54.

As the upper retainer 22 rotates, in a clockwise direction (as viewed in FIG. 2) from the first position 30 toward the second position 32, the side surfaces on the arms 106 (FIG. 7) on the upper retainer 22 approach the protrusions 80-86 (FIGS. 4 and 5) in the upper array 78 of protrusions. As the upper retainer 22 rotates into the second position 32 (FIG. 2) relative to the lower retainer 24, the side surfaces on the arms 106 move into engagement with the protrusions 80-86 in the upper array of protrusions. Therefore, the protrusions 80-86 are not deformed by the arms 106 as the upper retainer 22 rotates from the first position 30 to the second position 32. This means that the protrusions 80-86 are ineffective to provide significant resistance to relative rotation between the upper and lower retainers 22 and 24 during rotation of the upper retainer 22 from the first position 30 to the second position 32.

In addition, as the upper retainer 22 rotates in a clockwise direction from the first position 30 toward the second position 32, the ring 52 and web 54 are resiliently deflected. Therefore, the ring 52 and web 54 are effective to resist relative rotation between the upper and lower retainers 22 and 24 during rotation of the upper retainer 22 from the first position 30 to the second position 32. The web 54 has a thickness, measured in an axial direction, which at least partially determines the resistance to relative rotation between the upper and lower retainers 22 and 24 between the first and second positions 30 and 32.

As the upper retainer rotates in a clockwise direction from the first position 30 toward the second position 32, the ring 52 and web 54 are resiliently deflected. This results in the protrusions 88-91 in the lower array 87 of protrusions moving toward surfaces on the arms 116 (FIG. 4) of the lower projection 100. As the upper retainer 22 continues to rotate relative to the lower retainer 24 to the second position 32, the protrusions 88-91 in the lower array 87 of protrusions (FIG. 6) move into engagement with the surfaces on the arms 116 of the lower projection 100 (FIG. 4). Therefore, the protrusions 88-91 in the lower array 87 of protrusions are not deformed by the arms 116 as the upper retainer rotates from the first position 30 to the second position 32. This means that the protrusions 88-91 are ineffective to provide significant resistance to relative rotation between the upper and lower retainers 22 and 24 during rotation of the upper retainer 22 from the first position 30 to the second position 32.

As the upper retainer 22 continues to rotate in a clockwise direction from the second position 32 toward the third position 34, both the upper and lower arrays 78 and 87 of protrusions are resiliently deformed by the upper and lower projections 96 and 100 on the upper and lower retainers 22 and 24. Assuming the upper retainer 24 rotates relative to the lower retainer 22, the surfaces on the arms 106 of the upper retainer are pressed against and resiliently deform the protrusions 80-86 in the upper array 78 of protrusions. As this occurs, the ring 52 and web 54 are resiliently deflected. This presses the protrusions 88-91 in the lower array 87 of protrusions against surfaces on the arms 116 (FIG. 4) of the lower projection 100 to resiliently deform the lower array of protrusions. Therefore, rotation of the upper retainer 22 relative to the lower retainer 24 from the second position 32 to the third position 34 is resisted under the combined influence of the ring 52, web 54, upper array 78 of protrusions, and lower array 87 of protrusions.

The projections 96 and 100 extend vertically (as viewed in FIGS. 3-5) and radially into the recesses in the upper and lower arrays 78 and 87 of protrusions. The arms 106 (FIG. 7) of the upper projection 96 extend downward (as viewed in FIGS. 4 and 5) into the recesses 110 in the upper array 78 of protrusions. The arms 106 (FIG. 7) of the upper projection 96 also extend generally radially outward from the central portion 108 of the upper projection into the recesses 110 in the upper array 78 of protrusions.

Similarly, the arms 116 (FIG. 4) of the lower projection 100 extend upward (as viewed in FIGS. 4 and 5) into the recesses 120 (FIG. 6) in the lower array 87 of protrusions. The arms 116 (FIG. 4) of the lower projection 100 also extend generally radially outward from the central portion 118 of the lower projection into the recesses 120 (FIG. 6) in the lower array 87 of protrusions.

The projections 96 and 100 may have a construction which is different from the illustrated construction. For example, the central portion 108 (FIG. 7) of the upper projection 96 may be omitted and a plurality of separate arms 106 would form the projection. Similarly, the central portion 118 (FIG. 4) of the lower projection 100 may be omitted and a plurality of separate arms 116 would form the projection. Rather than being formed as elongated arms 106 and 116 each of, the projections 96 and 100 may be formed by a plurality of series of separate projections. Each series of separate projections would have a length which is approximately the same as their height. Although the projections 96 and 100 are identical, they may have different configurations if desired.

The intermediate section 26 may have a construction which is different than the construction illustrated in FIGS. 4-7. For example the lower array 87 (FIG. 6) of protrusions may be eliminated and the lower side surface 76 (FIG. 5) of the web 54 aligned with the lower side surface 64 of the ring 52. The lower projection 100 could be eliminated and the lower side surface 76 of the web 54 would be secured to the lower retainer 24 along with the lower side surface 64 of the ring 52. Of course, rather than eliminating the lower array 87 of protrusions, the upper array 78 of protrusions may be eliminated and the upper side surface 74 of the web 54 secured to the upper retainer 22.

As another example of a different construction for the intermediate section 26, the web 54 may be eliminated. If this is done the protrusions 80-86 and 88-91 may be extended further toward a central portion of the ring 52. If desired, radially inner end portions of the protrusions 80-86 and 88-91 may be interconnected. Regardless of whether or not the radially inner end portions of the protrusions 80-86 and 88-91 are interconnected, the upper array 78 of protrusions may be formed as a continuation of the lower array 87 of protrusions.

If desired, a greater or lesser number of protrusions may be provided in the upper and lower arrays 78 and 87 of protrusions. This is true whether the web 54 is eliminated or maintained. If the web 54 is maintained, one or more openings may be provided in the web. Of course, a greater or lesser number of arms may be provided on the upper and lower projections 96 and 100.

The protrusions 80-86 and 88-91 may be formed with a configuration which is different from the configuration illustrated in FIGS. 4-6. For example, the protrusions 80-86 and 88-91 may be lengthened to extend further toward the center of the ring 52. Of course, the configuration of the projections 96 and 100 may be changed to accommodate any changes in the configuration of the protrusions. The protrusions 80-86 in the upper array 78 of protrusions may have a configuration which is different than the configuration of the protrusions 88-91 in the lower array 87 of protrusions.

The intermediate section 26 is integrally formed as one piece. Thus, the intermediate section 26 is molded as a single piece of polymeric material. The polymeric material may be a urethane silicon blend manufactured by The Polymer Technology Group having a place of business in Berkley, Calif. Of course, the intermediate section may be formed of a different material if desired. The components of the intermediate section 26 may be formed separately and interconnected to form a unitary intermediate section. It is contemplated that the components of the intermediate section 26 may be formed of different materials.

The upper and lower retainers 22 and 24 are each integrally molded as one piece of titanium. Of course, the upper and lower retainers 22 and 24 may be formed of other materials which are biocompatible. Although it is preferred to integrally mold the retainers 22 and 24 as one piece, the projections 96 and 100 may be formed separately and connected to the retainers if desired. The illustrated projections 96 and 100 are rigid and cooperate with resiliently flexible protrusions 80-86 and 88-91. However, the projections 96 and 100 may be resiliently flexible if desired and cooperate with resiliently flexible protrusions 80-86 and 88-91. Alternatively the projections may be resiliently flexible and the protrusions rigid.

In the embodiment of the invention described herein, the projections 96 and 100 are initially spaced from the protrusions 80-86 and 88-91. However, if desired, the projections 96 and 100 may initially be disposed in engagement with the protrusions 80-86 and 88-91. For example, a portion of each side surface on an arm 106 of the projection 96 may initially be disposed in engagement with one of the protrusions 80-86. If this is done, opposite side surfaces on an arm 106 would be disposed in engagement with two adjacent protrusions, for example the protrusions 80 and 82.

The illustrated retainers 22 and 24 have circular central openings. However, the central openings may be eliminated and/or additional openings formed in the retainers 22 and 24.

Figure 8:
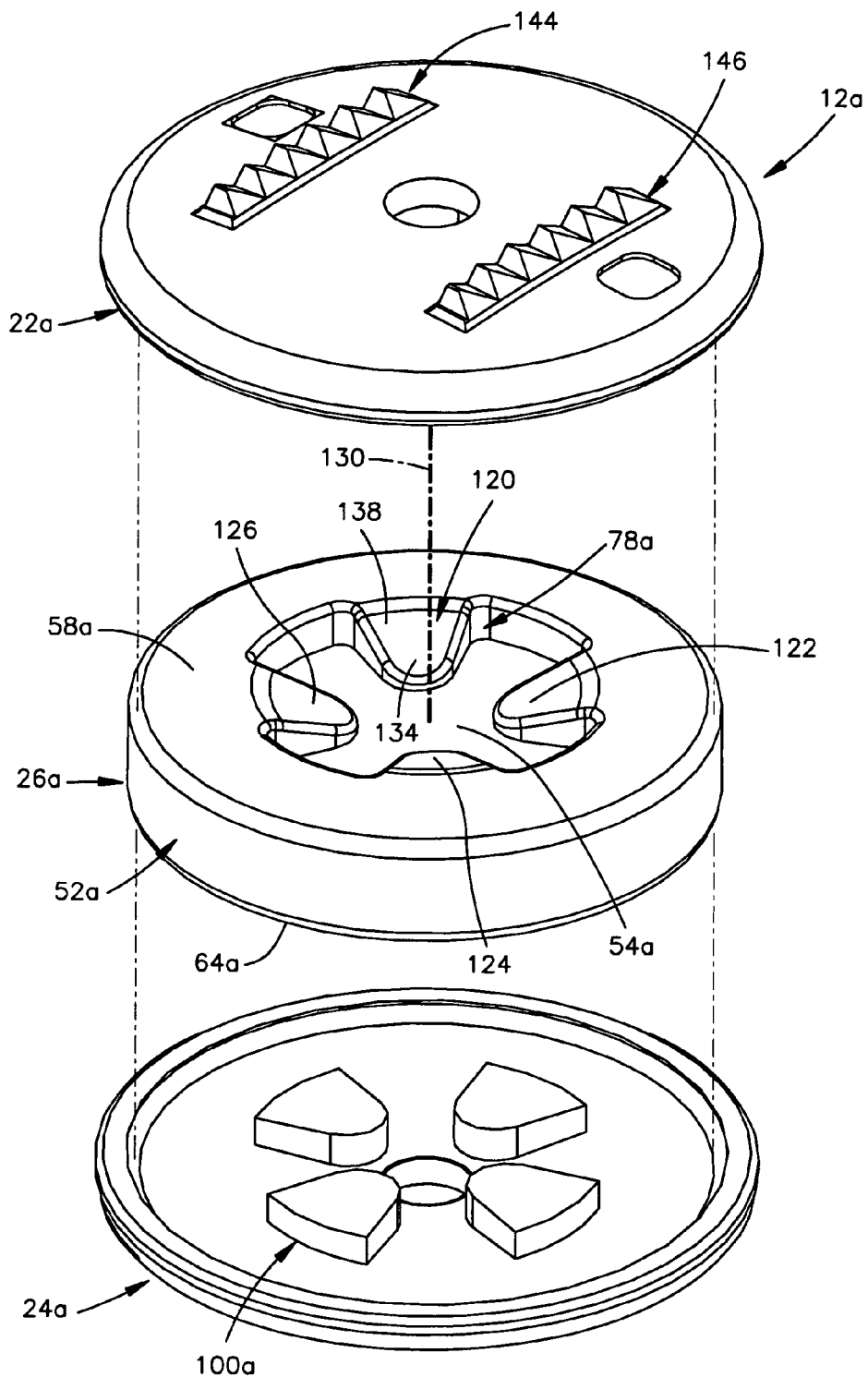
FIG. 8 is an exploded, schematic perspective illustration, generally similar to FIG. 4, illustrating a second embodiment of the artificial disc.
Figure 9:
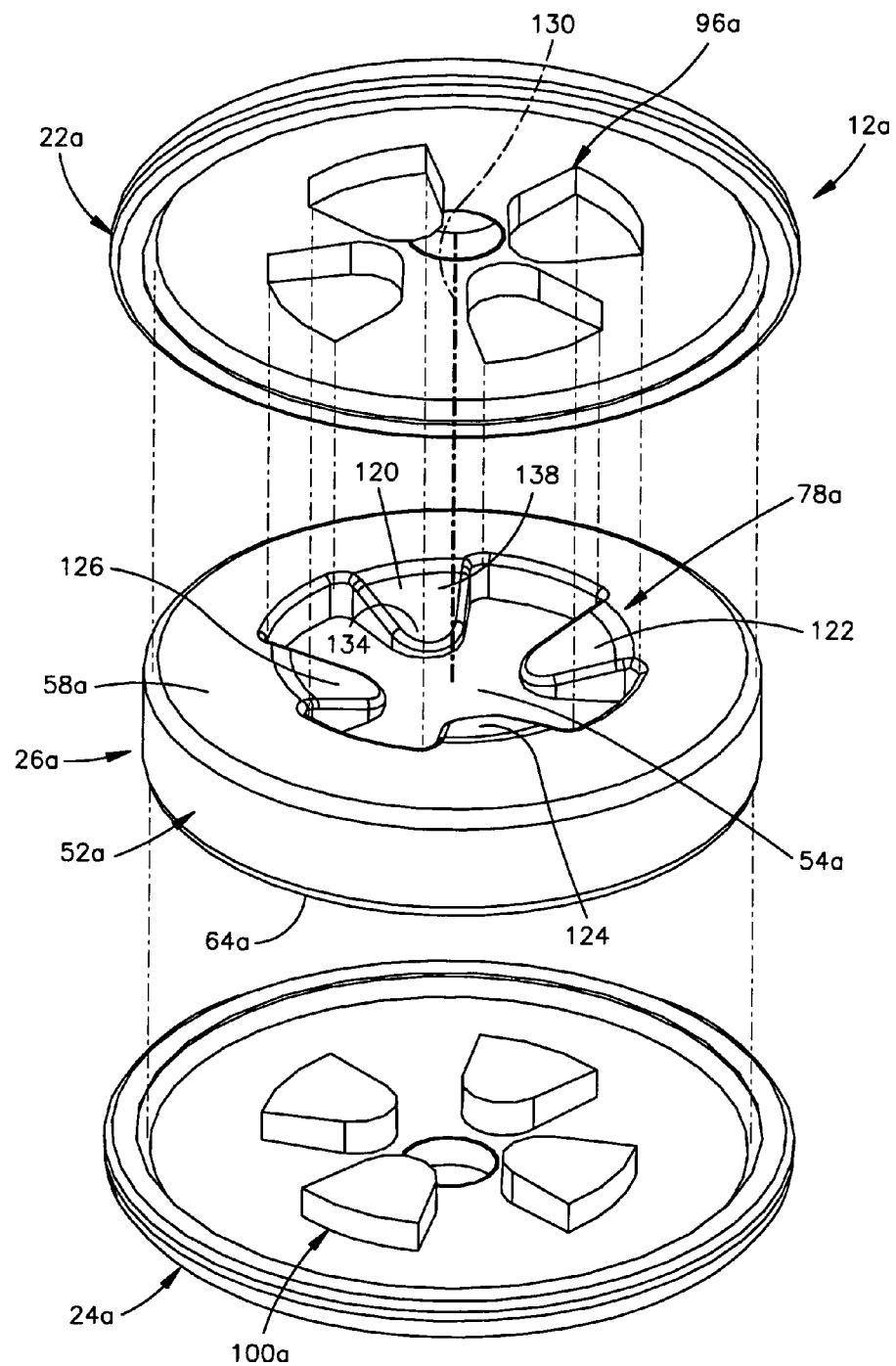
FIG. 9 is an exploded, schematic perspective illustration further illustrating the artificial disc of FIG. 8.

In the embodiment of the invention illustrated in FIGS. 1-7, the protrusions in the upper and lower arrays 78 and 87 of protrusions have the same thickness as measured perpendicular to the side surfaces 74 and 76 of the web 54, throughout the extent of the protrusions. In the embodiment of the invention illustrated in FIGS. 8 and 9, the protrusions have a thickness which varies along the radial length of the protrusions. Since the embodiment of the invention illustrated in FIGS. 8 and 9 is generally similar to the embodiment of the invention illustrated in FIGS. 1-7, similar numerals will be utilized to identify similar components, the suffix letter "a" being added to the numerals of FIGS. 8 and 9 to avoid confusion.

An artificial disc 12a is utilized to replace a damaged spinal disc in a spinal column. The artificial disc 12a is positioned between vertebra 16 and 18 (FIG. 3) in the same manner as is the artificial disc 12 of FIGS. 1-7.

The artificial disc 12a (FIG. 7) includes an upper retainer 22a and a lower retainer 24a. A resiliently deflectable intermediate section 26a is fixedly connected with the rigid upper and lower retainers 22a and 24a and is effective to resist relative rotation between the upper and lower retainers. In addition, the intermediate section 26a resists and cushions vertical movement between the upper and lower retainers 22a and 24a.

The intermediate section 26a (FIGS. 7 and 8) includes a ring 52a having an upper side surface 58a which is fixedly connected to the upper retainer 22a. Similarly, the ring 52a has a lower side surface 64a which is fixedly connected to the lower retainer 24a.

The ring 52a (FIGS. 8 and 9) extends around and encloses a web 54a. Upper and lower arrays of protrusions extend from the web 54a toward the upper retainer 22a and lower retainer 24a. The upper array 78a of protrusions includes protrusions 120, 122, 124 and 126 (FIG. 9). Although only the upper protrusions 120-126 are illustrated in FIGS. 8 and 9, it should be understood that there is a lower array of protrusions having the same construction as the upper array of protrusions. The lower array of protrusions is vertically aligned with and has the same configuration as the upper array of protrusions.

The protrusions 120-126 all have the same tapering configuration. A protrusion 120 has a central axis 130 (FIG. 8) which extends through a vertical central axis of the intermediate section 26a. The central axis 130 of the protrusion 120 is coincident with a central axis of the protrusion 124. The thickness of the protrusion 120 varies along the radial length of the protrusion.

The protrusion 120 has a radially inner end portion 134 with a relatively small thickness, as measured along an axis extending perpendicular to the web 54a. A radially outer end portion 138 has a relatively large thickness, as measured along an axis extending perpendicular to the web 54a. The thickness of the protrusion 120 continuously varies along the length of the protrusion.

In the embodiment of the invention illustrated in FIGS. 8 and 9, the protrusion 120 has an inner end portion 134 with a relatively small thickness and an outer end portion 138 with a relatively large thickness. If desired, the inner end portion 134 could have a relatively large thickness and the outer end portion 138 may have a relatively small thickness. The illustrated embodiment of the protrusions 120-126 have smoothly tapering major and minor side surfaces. If desired, one or more of the side surfaces could taper in a stepwise manner. The illustrated protrusions 120-126 have a relatively small circumferential extent at their inner end portions 134 and a relatively large circumferential extent at their outer end portions 138. If desired, the protrusions 120-126 could have a relatively large circumferential extent at their inner end portions 134 and a relatively small circumferential extent at their outer end portions 138.

The intermediate section 26a is integrally molded as one piece of a resilient polymeric material. Specifically, the one piece intermediate section 26a is molded of a urethane silicon blend which is commercially available from Polymer Technology Group having a place of business in Berkley, Calif. Of course, the intermediate section 26a may be molded of a different polymeric material if desired. The resiliently flexible intermediate section 26a is integrally molded as a single piece. However, the intermediate section 26a may be formed of a plurality of pieces which are interconnected. For example, the protrusions 120-126 may be formed separately from the web 54a and ring 52a. The web 54a and protrusions 120-126 may be formed of different materials if desired.

A plurality of upper projections 96a (FIG. 9) are integrally formed as one piece with the upper retainer 22a and are disposed between the protrusions 120-126. Similarly, a plurality of lower projections 100a are integrally formed with the lower retainer 24a and are disposed between projections of the lower group of projections. The upper projections 96a and the lower projections 100a have the same configuration and are vertically aligned with each other.

When the upper and lower retainers 22a and 24a are in a first position relative to each other, that is in a position corresponding to the first position 30 of FIG. 2, the projections 96a and 100a are spaced from protrusions in the upper and lower arrays of protrusions. Upon relative rotation between the upper and lower retainers 22a and 24a from the first position to the second position, the upper and lower projections 100a and 96a move from a position spaced from protrusions in the upper and lower arrays of protrusions to a position engaging the protrusions. At this time, the upper retainer 22a will have rotated relative to the lower retainer 24a to a position corresponding to the second position 32 in FIG. 2.

Rotational movement of the upper retainer 22a relative to the lower retainer 24a from the first position to the second position is resisted by the ring 52a and web 54a. Thus, the ring 52a and web 54a are resiliently deflected as the upper retainer 22a is rotated relative to the lower retainer 24a. Continued rotation of the upper retainer 22a relative to the lower retainer 24a from a second position, corresponding to the position 32 of FIG. 2 to a third position, corresponding to the position 34 of FIG. 2 is effective to cause the projections 100a and 96a to resiliently deflect or deform the upper and lower arrays of protrusions.

The upper retainer 22a is provided with a first set 144 (FIG. 8) of teeth and a second set 146 of teeth. It should be understood that the lower side of the lower retainer 24a is provided with teeth which correspond to the two sets 144 and 146 of teeth. The teeth on the upper and lower retainers 22a and 24a facilitate connecting the retainers with the vertebrae 16 and 18. It should be understood that the teeth on the upper and lower retainers 22a and 24a may be omitted if desired. It should also be understood that teeth, similar to the two sets 144 and 146 of teeth, may be provided on the upper and lower retainers 22 and 24 of FIGS. 1-7 if desired.

In the foregoing description, only the movement of the retainer 22a in a clockwise direction relative to the lower retainer 24a has been described. However, the upper retainer 22a may be rotated in a counterclockwise direction relative to the lower retainer 24a in the same manner as is illustrated schematically in FIG. 2 for the upper and lower retainers 22 and 24.

In view of the foregoing description, it is apparent that the present invention provides a new and improved artificial disc 12 to replace a damaged spinal disc in a spinal column. The artificial disc 12 includes a first or upper retainer 22 which is engagable with a first vertebra 16 and a second or lower retainer 24 which is engagable with a second vertebra 18. An intermediate section 26 is connected with the upper and lower retainers 22 and 24. The intermediate section 26 of the artificial disc 12 resists relative rotation between the upper and lower retainers 22 and 24.

The intermediate section 26 includes a first portion 46 which resists relative rotation between the upper and lower retainers 22 and 24 from a first position 30 to a second position 32. A second portion 48 of the intermediate section 26 resists relative rotation between the upper and lower retainers 22 and 24 from the second position 32 to a third position 34. The second portion 48 of the intermediate section 26 of the artificial disc 12 is ineffective to provide significant resistance to relative rotation between the upper and lower retainers 22 and 24 from the first position 30 to the second position 32.

The intermediate section 26 of the artificial disc may include a ring 52 which is connected with the upper and lower retainers to resist relative rotation between the retainers. A plurality of protrusions 80-91 may extend inwardly from the ring 52 toward a central portion of the intermediate section 26. A plurality of the projections 96 and 100 on the retainers 22 and 24 are engagable with the protrusions 80-91. The projections 96 and 100 on the retainers 22 and 24 may have longitudinal axes which extend from central portions 108 and 118 of the retainers 22 and 24 toward peripheral portions 71 and 72 of the retainers 22 and 24.

From the above description of the invention, those skilled in the art will perceive improvements, changes and modifications. Such improvements, changes and modifications within the skill of the art are intended to be covered by the appended claims.

Having described the invention, the following is claimed:

1. An artificial disc to replace a damaged spinal disc in a spinal column, said artificial disc comprising:
a first retainer engagable with a first vertebra;
a second retainer engagable with a second vertebra; and
an intermediate section disposed between and connected with said first and second retainers, said intermediate section includes a first portion which resists relative rotation between said first and second retainers from a first position of said first retainer relative to said second retainer to a second position of said first retainer relative to said second retainer and a second portion which resists relative rotation between said first and second retainers from said second position of said first retainer relative to said second retainer to a third position of said first retainer relative to said second retainer, said second portion of said intermediate section being ineffective to provide significant resistance to relative rotation between said first and second retainers during rotation of said first retainer relative to said second retainer from the first position to the second position.

2. An artificial disc as set forth in claim 1 wherein said first and second portions of said intermediate section are integrally formed as one piece.

3. An artificial disc as set forth in claim 1 wherein said second portion of said intermediate section includes a plurality of protrusions which engage a plurality of projecting surfaces on one of said retainers during relative rotation between said first and second retainers from said second position to said third position, said protrusions on said intermediate section being spaced from said projecting surfaces on said one of said retainers during relative rotation between said first and second retainers from said first position to said second position.

4. An artificial disc as set forth in claim 1 wherein said first portion of said intermediate section includes a ring which extends around said second portion of said intermediate section, said ring being connected to said first and second retainers.

5. An artificial disc as set forth in claim 4 wherein said first retainer includes a plurality of projecting surfaces which are at least partially enclosed by said ring.

6. An artificial disc as set forth in claim 1 wherein said first and second retainers are formed of metal and said intermediate section is formed of a polymeric material.

7. An artificial disc as set forth in claim 1 wherein said second portion of said intermediate section includes recesses which have a first plurality of openings which are disposed adjacent to said first retainer and a second plurality of openings which are disposed adjacent to said second retainer, said first retainer includes a first plurality of projecting surfaces which extend into said first plurality of openings, said second retainer includes a second plurality of projecting surfaces which extend into said second plurality of openings.

8. An artificial disc as set forth in claim 7 wherein said first plurality of projecting surfaces includes a first side surface area which faces toward and is spaced from a first side surface area of a first one of said recesses when said first retainer is in the first position relative to said second retainer, said first plurality of projecting surfaces includes a second side surface area which faces toward and is spaced from a second side surface area of said first one of said recesses when said first retainer is in the first position relative to said second retainer, said second plurality of projecting surfaces includes a first side surface area which faces toward and is spaced from a first side surface area on a second one of said recesses when said first retainer is in the first position relative to said second retainer, said second plurality of projecting surfaces includes a second side surface area which faces toward and is spaced from a second side surface area on said second one of said recesses when said first retainer is in the first position relative to said second retainer.

9. An artificial disc as set forth in claim 7 wherein each of said recesses has an opening which faces toward a central axis of said intermediate section, each projecting surface of said first plurality of projecting surfaces extends outward from a central portion of said first retainer through one of said openings and into one of said recesses, each projecting surface of said second plurality of projecting surfaces extends outward from a central portion of said second retainer through one of said openings and into one of said recesses.

10. An artificial disc as set forth in claim 7 wherein said recesses have openings which face toward said first retainer and openings which face toward said second retainer, said first plurality of projecting surfaces extend from said first retainer toward said second retainer and into said recesses, said second plurality of projecting surfaces extend from said second retainer toward said first retainer and into said recesses.

11. An artificial disc as set forth in claim 1 wherein said first portion of said intermediate section includes a first surface which is fixedly connected to said first retainer and is stationary relative to said first retainer during relative rotation between said first and second retainers, said first portion of said intermediate section includes a second surface which is fixedly connected to said second retainer and is stationary relative to said second retainer during relative rotation between said first and second retainers.

12. An artificial disc to replace a damaged spinal disc in a spinal column, said artificial disc comprising:
a first retainer engagable with a first vertebra, said first retainer including a projection having at least one arm, each arm having a projecting surface which is disposed adjacent an inner surface of said first retainer, each arm having a longitudinal axis which extends radially outward from a central portion of said first retainer toward a peripheral portion of said first retainer and perpendicular to a central axis of the artificial disc;
a second retainer engagable with a second vertebra and having an inner surface, and
an intermediate section disposed between said first and second retainers and immovably fixed to said inner surface of said second retainer, said intermediate section includes a recess into which said projecting surface extends, each projecting surface being movable relative to surfaces defining the recess.

13. An artificial disc as set forth in claim 12 wherein said intermediate section includes an array of protrusions which extend inwardly from a peripheral portion of said intermediate section toward a central axis of said intermediate section and which at least partially define a plurality of recesses, said projection of said first retainer having a plurality of arms defining a plurality of projecting surfaces which extend into said plurality of recesses.

14. An artificial disc as set forth in claim 13 wherein each of said protrusions of said array of protrusions includes an outer portion which is connected with said peripheral portion of said intermediate section and an inner portion which is spaced from said peripheral portion of said intermediate section.

15. An artificial disc as set forth in claim 14 wherein said outer portion of each of said protrusions of said array of protrusions has a first thickness as measured in a direction parallel to the central axis of said intermediate section and said inner portion of each of said protrusions of said array of protrusions has a second thickness as measured in a direction parallel to the central axis of said intermediate section, said second thickness being less than said first thickness.

16. An artificial disc as set forth in claim 12 wherein said intermediate section includes a first portion which resists relative rotation between said first and second retainers from a first position of said first retainer relative to said second retainer to a second position of said first retainer relative to said second retainer and a second portion which resists relative rotation between said first and second retainers from said second position of said first retainer relative to second retainer to a third position of said first retainer relative to said second retainer, said second portion of said intermediate section being ineffective to provide significant resistance to relative rotation between said first and second retainers during rotation of said first retainer relative to said second retainer from the first position to the second position.

17. An artificial disc as set forth in claim 12 wherein said second retainer includes a second projecting surface which is disposed adjacent an inner surface of said second retainer and which has a longitudinal axis which extends from a central portion of said second retainer toward a peripheral portion of said second retainer, said intermediate section includes a second recess into which said second projecting surface extends.

18. An artificial disc as set forth in claim 12 wherein said at least one arm comprises a plurality of arms defining a plurality of projecting surfaces which are disposed adjacent said inner surface of said first retainer and which have longitudinal axes which extend radially outward from a central portion of said first retainer toward a peripheral portion of said first retainer, said recess of said intermediate section is one of a plurality of recesses into which said plurality of projecting surfaces extends.

19. An artificial disc as set forth in claim 18 wherein said second retainer includes a second plurality of projecting surfaces which are disposed adjacent an inner surface of said second retainer and which extend from a central portion of said second retainer toward a peripheral portion of said second retainer, said intermediate section includes a second plurality of recesses into which said second plurality of projecting surfaces extend.

20. An artificial disc to replace a damaged spinal disc in a spinal column, said artificial disc comprising:
a first retainer engagable with a first vertebra;
a second retainer engagable with a second vertebra;
an intermediate section disposed between and connected with said first and second retainers, said intermediate section includes a ring which is connected with said first and second retainers and is effective to resist relative rotation between said first and second retainers, a web which is enclosed by said ring and is spaced from said first and second retainers, a first plurality of protrusions which extend inwardly from said ring toward a central portion of said web at spaced apart locations along a first side of said web and adjacent to said first retainer, and a second plurality of protrusions which extend inwardly from said ring toward the central portion of said web at spaced apart locations on a second side of said web and adjacent to said second retainer, said first retainer including a first plurality of projecting surfaces which are engagable with protrusions of said first plurality of protrusions, said second retainer including a second plurality of projecting surfaces which are engagable with protrusions of said second plurality of protrusions.

21. An artificial disc as set forth in claim 20 wherein said ring, web, first plurality of protrusions, and second plurality of protrusions are all integrally formed as one piece of polymeric material.

22. An artificial disc as set forth in claim 20 wherein said ring has a first side which is connected to said first retainer and a second side which is connected to said second retainer, said first side of said web faces toward said first retainer and is offset from said first side of said ring in a direction toward said second retainer, said second side of said web faces toward said second retainer and is offset from said second side of said ring in a direction toward said first retainer, said first plurality of protrusions extend from said first side of said web toward said first retainer and said second plurality of protrusions extend from said second side of said web toward said second retainer.

23. An artificial disc as set forth in claim 22 wherein each protrusion of said first plurality of protrusions is at least partially defined by an arcuate side surface which extends transverse to said first side of said web and has a center of curvature which is spaced from a central axis of said web, each protrusion of said second plurality of protrusions is at least partially defined by an arcuate side surface which extends transverse to said second side of said web and has a center of curvature which is spaced from the central axis of said web.

24. An artificial disc as set forth in claim 22 wherein each protrusion of said first plurality of protrusions has a uniform thickness as measured along an axis extending perpendicular to said first side of said web, each protrusion of said second plurality of protrusions has a uniform thickness as measured along an axis extending perpendicular to said second side of said web.

25. An artificial disc as set forth in claim 22 wherein each protrusion of said first plurality of protrusions has a first thickness adjacent to a central portion of said web and a second thickness adjacent to said ring, said first thickness being less than said second thickness, each protrusion of said second plurality of protrusions has a third thickness adjacent to a central portion of said web and a fourth thickness adjacent to said ring, said third thickness being less than said fourth thickness.

26. An artificial disc as set forth in claim 20 wherein said ring resists relative rotation between said first and second retainers from a first position of said first retainer relative to said second retainer to a second position of said first retainer relative to said second retainer, said first and second pluralities of protrusions resist relative rotation between said first and second retainers from said second position of said first retainer relative to said second retainer to a third position of said first retainer relative to said second retainer, said first and second protrusions being ineffective to provide significant resistance to relative rotation between said first and second retainers during rotation of said first retainer relative to said second retainer from the first position to the second position.

27. An artificial disc as set forth in claim 26 wherein said first and second pluralities of projecting surfaces are disposed in engagement with said first and second pluralities of protrusions during rotation of said first retainer relative to said second retainer from said second position of said first retainer relative to said second retainer to said third position of said first retainer relative to said second retainer.

28. An artificial disc as set forth in claim 12 wherein said intermediate section includes a surface immovably fixed to said inner surface of said second retainer such that said surface of said intermediate section and said inner surface of said second retainer do not move relative to one another during rotation of said first retainer relative to said second retainer.

29. An artificial disc as set forth in claim 12 wherein said intermediate section is immovably fixed to said inner surface of said first retainer.

30. An artificial disc as set forth in claim 12 wherein said intermediate section includes a surface immovably fixed to said inner surface of said first retainer such that said surface of said intermediate section and said inner surface of said first retainer do not move relative to one another during rotation of said first retainer relative to said second retainer.

* * * * *